(12) United States Patent
Courteix

(10) Patent No.: US 6,719,732 B2
(45) Date of Patent: Apr. 13, 2004

(54) PROTECTION DEVICE FOR SYRINGE NEEDLE

(75) Inventor: Serge Courteix, Osny (FR)

(73) Assignee: Rumpler Technologies, La Courneuve (FR)

(*) Notice: Subject to any disclaimer, the term of this patent is extended or adjusted under 35 U.S.C. 154(b) by 69 days.

(21) Appl. No.: 09/991,862

(22) Filed: Nov. 14, 2001

(65) Prior Publication Data

US 2002/0062108 A1 May 23, 2002

(30) Foreign Application Priority Data

Nov. 17, 2000 (FR) ............................... 00 14843

(51) Int. Cl.⁷ ............................... A61M 5/32
(52) U.S. Cl. ................. 604/192; 604/263; 604/198
(58) Field of Search ............................... 604/110, 171, 604/181, 187, 188, 192–199, 263; 128/919

(56) References Cited

U.S. PATENT DOCUMENTS

| 4,986,818 A | 1/1991 | Imbert et al. | |
| 6,551,286 B1 * | 4/2003 | Claessens | 604/263 |

FOREIGN PATENT DOCUMENTS

| EP | 0 229204 A1 | 7/1987 | ............ A61M/5/32 |
| EP | 0 592 814 A2 | 4/1994 | ............ A61M/5/32 |
| FR | 2 777 787 | 10/1999 | ............ A61M/5/32 |

* cited by examiner

Primary Examiner—Manuel Mendez
Assistant Examiner—Kevin C. Sirmons
(74) Attorney, Agent, or Firm—Cohen, Pontani, Lieberman & Pavane

(57) ABSTRACT

This invention relates to a protection device for a syringe needle comprising an elastic needle cap of general longitudinal direction presenting a closed distal end and an open proximal end, said cap being formed by a lateral wall defining an inner housing intended to receive the distal part of the body of a needle syringe, and by an end wall capable of being pierced through a part of its thickness by the free end of said needle. The housing comprises, from said proximal end, an opening, a first portion, a second portion intended to house the distal part of the syringe body which bears said needle, and a third portion which narrows from said second portion in the direction of the back of said housing. The lateral wall is further provided with an annular bead disposed in said housing between said first and second portions of said housing.

14 Claims, 4 Drawing Sheets

PROTECTION DEVICE FOR SYRINGE NEEDLE

FIELD OF THE INVENTION

The present invention relates to a device for protecting the needle of a syringe comprising an elastic needle cap.

More precisely, this invention relates to a protection device for syringe needle of the type comprising an elastic needle cap of generally longitudinal direction presenting a closed distal end and an open proximal end, said cap being formed by a lateral wall extending from said proximal end along a proximal end zone defining an inner housing intended for receiving the distal part of the body of a needle syringe, and by an end wall whose thickness extends from said distal end along a distal end zone, said end wall being capable of being pierced over a part of its thickness by the free end of said needle, the housing comprising, from said proximal end, an opening presenting a maximum diameter, a first portion of truncated or cylindrical shape of circular cross-section, a second cylindrical portion of circular cross-section presenting a diameter smaller than the maximum diameter and intended to house the distal part of the syringe body which bears said needle, and a third portion which narrows from the second portion as far as the back of said housing.

BACKGROUND OF THE INVENTION

Syringe needle protection devices of the afore-mentioned type have already been proposed.

For example, Patent EP 0 429 052 relates to a needle shielding assembly comprising, as is visible in FIG. 5, an elastic needle sheath similar to the elastic needle cap defined hereinabove.

However, this type of needle protection device presents a certain number of drawbacks.

The protection device for syringe needle forming the subject matter of the present invention is intended to be mounted on a hypodermic syringe for injecting a medicinal liquid into a patient.

Whether such hypodermic syringes are pre-filled or are to be filled by the hospital staff just before the injection is effected, these syringes must remain sterile until they are used.

For example, when the syringe is packaged when already filled with liquid, the following different steps are effected for preparing the syringe before it is packaged. In the first place, the body of the syringe, on the distal part of which is mounted a needle coated with a silicone coating, is washed. An elastic needle cap is then mounted on the needle to form an assembly which will subsequently be rendered sterile, preferably by passage in an autoclave.

After passage of the afore-mentioned assembly in an autoclave, the syringe is filled with the liquid which is intended for it and the syringe body is closed by the piston and plunger which complete the syringe before subsequent packaging thereof.

During passage in the autoclave, as the elastic needle cap is made of a material allowing the passage of gases (generally rubber), it is possible to make a pressure equilibrium between the outside of the elastic cap, i.e. the enclosure of the autoclave, and the interior of the elastic cap, i.e. the housing receiving the needle of the syringe.

During the cycle of sterilization in an autoclave, apart from an increase in the temperature in the enclosure of the autoclave, a considerable increase in the pressure is also conventionally effected after one or more partial vacuums in the enclosure (for example up to 2.3 bars). This maximum pressure is maintained for a certain time (pressure plateau) before a fresh partial vacuum is made in the enclosure of the autoclave. At the end of the cycle, the pressure is increased up to atmospheric pressure, while the temperature redescends progressively down to ambient temperature.

From the preceding explanations, it will be understood that, during the cycle of sterilization in an autoclave, there are fairly sudden pressure changes in the enclosure. For example, upon the sudden drop in pressure in the enclosure between the maximum pressure value and the partial vacuum, it happens that the pressure in the housing of the elastic cap cannot be balanced quickly enough, resulting in a momentary residual pressure in this housing which presents a value greater than that of the pressure prevailing in the enclosure.

In certain cases, particularly when the lateral wall of the elastic cap is not sufficiently resistant, the residual pressure present in the housing generates a deformation of this lateral wall which may lead to the relative displacement of the elastic cap with respect to the distal part of the syringe body on which the cap is mounted. Such displacement of the cap may even be so great that it may lead to a separation between the cap and the syringe body when the deformation undergone by the cap does not make it possible to retain the distal part of the syringe body in the housing.

In the case of the displacement between the cap and the syringe body, there may exist a rupture of tightness between the housing of the cap and the environment outside the cap, which induces a risk of loss of sterility in this housing, therefore of the needle. The loss of sterility is confirmed in the case of the separation between the cap and the syringe body.

Such displacement also induces a risk of leakage of liquid from the syringe, hence a dose of liquid in the syringe whose volume has decreased and a risk of contact with this liquid for the user, which may prove dangerous in the case of certain liquids used for examinations, particularly in medical imagery. Likewise, the contacting of the free end of the needle with the outside environment may generate physico-chemical reactions on the liquid, such as crystallization or coagulation, capable of degrading this liquid and of rendering the syringe unusable.

This risk of loss of sterility is all the greater in the case of the syringe body being made of glass, as the use of this material involves a range of dimensional tolerance much broader than in the case of a syringe made of plastics material.

The present invention has for its object to provide a protection device for syringe needle which does not present the drawbacks set forth hereinbefore, i.e. guaranteeing that the needle is maintained in a tightly closed sterile atmosphere until it is used, while conserving, and even improving, the facility of removal of the protection device by the user before the syringe is used.

SUMMARY OF THE INVENTION

This object is attained by a protection device for syringe needle of the type mentioned hereinabove, which is characterized in that the lateral wall of the cap is further provided with an annular bead disposed in said housing between said first and second portions of said housing, at least one slot extending longitudinally over said annular bead.

It will be understood that this annular bead makes it possible to retain the distal part of the syringe body in the housing of the cap, especially when there is a residual pressure inside this housing, the annular bead in that case constituting a mechanical retaining means preventing a relative displacement in longitudinal translation between the cap and the distal part of the syringe body. Said slot or slots facilitate the passage of the gases under pressure (in particular water vapor under pressure used during the passage in an autoclave and which effects sterilization) between the housing of the cap and the outside of the cap. In this way, a greater deformability of the annular bead in the housing is also obtained, which makes it possible to minimize the necessary tearing force when the cap and the syringe body are separated.

This annular bead is all the more efficient for retaining the distal part of the syringe body in the housing as this distal part is most often made in the form of a swell which may present a general shape of a ball or section of sphere. This swell presents, in its median part, a greater diameter than the part of revolution, often truncated, which is adjacent thereto. In this way, the annular bead is naturally housed in the annular depression formed on the distal part of the syringe body, between the swell forming the median part of the distal part and the part of revolution which is adjacent to the distal part.

According to an advantageous characteristic, said bead presents in longitudinal section the form of a half drop of water of which the widest part is turned in the direction of the proximal end of the cap. This shape is particularly adapted to retain the distal port of the syringe body in the housing during the passage in an autoclave while also allowing an easy separation between the cap and the body of the needle, this separation step preceding the use of the syringe.

The outer face of the lateral wall which surrounds the annular bead is preferably in the form of a frustum of a cone.

Furthermore, according to another embodiment of the invention, the protection device for syringe needle is provided also to comprise a rigid shell of general longitudinal cylindrical shape, of circular cross-section, presenting an open proximal end and an at least partially closed distal end, said shell comprising a longitudinal wall extending from said proximal end up to said distal end and a terminal wall located at its distal end, said shell being intended to surround and contain said elastic needle cap, and being provided with means for retaining said cap.

The main purpose of the additional use of a rigid shell surrounding the elastic cap is to protect all persons who successively manipulate the syringe from an accidental prick with the needle if the free end of the needle completely pierces the end wall of the elastic needle cap.

This rigid shell also presents the advantage of facilitating manipulation of the syringe needle protection device by the machines of the production and assembly lines, particularly when the protection device is mounted on the syringe.

BRIEF DESCRIPTION OF THE DRAWINGS

The invention will be more readily understood on reading the following description of embodiments thereof given by way of non-limiting example with reference to the accompanying drawings in which.

DESCRIPTION OF PREFERRED EMBODIMENTS

Figure 1:
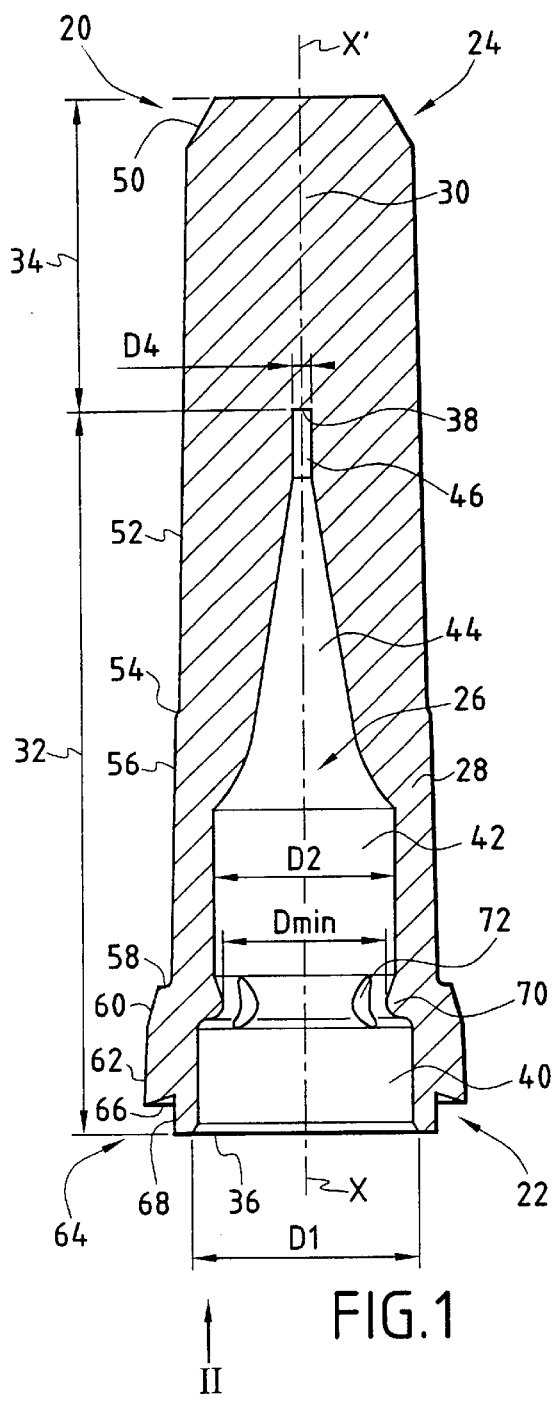
FIG. 1 is a view in diametral longitudinal section of a protection device for syringe needle according to the present invention, comprising an elastic needle cap.

In the following description, the adjective "distal" refers to the part most remote from the hand of the person holding the syringe, and the adjective "proximal" refers to the part closest to the hand of the person holding the syringe.

Referring now to the drawings, FIGS. 1 to 5 show a device for protecting a syringe needle composed of an elastic needle cap 20 extending in a longitudinal direction (X, X') between an open proximal end 22 and a closed distal end 24. The cap 20 defines an inner housing 26 delimited by a lateral wall 28 and by an end wall 30.

The lateral wall 28 extends, in the longitudinal direction along axis (X, X'), from the proximal end 22 along a proximal end zone 32 representing about two thirds of the length of the cap 20.

The end wall 30 is therefore solid and extends, in the longitudinal direction along axis (X, X'), from the distal end 24 along a distal end zone 34 representing about one third of the total length of the cap 20. In this way, the thickness of the end wall 30 (which corresponds to the length of the distal end zone 34) allows the housing of the free end of the needle of a syringe, as will be explained hereinafter.

As is conventional for this type of needle protection device, the elastic cap 20 is of revolution about the longitudinal axis (X, X'). This symmetry of revolution concerns the outer contour of the cap 20 (lateral wall 28 and end wall 30), as well as the inner contour of the lateral wall 28 which defines the housing 26, except concerning the presence of slots, as will be explained hereinafter.

The inner housing 26 is composed of a plurality of portions extending from an opening 36 located at the proximal end 22 of the cap 20, up to a back 38 located on the other side of the proximal end zone 32.

Adjacent to the opening 36, the housing 26 comprises a first portion 40 which presents a cylindrical form of circular cross-section, of axis (X, X') in the Figures, a truncated shape narrowing in the direction of the back 38 also being able to be used.

As illustrated, the first portion 40 presents a diameter substantially equal to the diameter D1 of the opening 36.

On the other side of the opening 36, the afore-mentioned first portion 40 is adjacent a second portion 42 intended to receive the distal part of a syringe body which bears the needle, this second portion presenting a cylindrical shape of circular cross-section and of longitudinal axis (X, X') and presenting a diameter D2 smaller than the diameter D1 of the opening 36.

In the direction opposite the first portion 40, the second portion 42 is extended by a third tapering portion 44 whose diameter narrows progressively in the direction of the back 38 of the housing 26. At the level of the back 38 of the housing 26, there is constituted a fourth cylindrical portion 46 of circular cross-section presenting a diameter D4 substantially equal to the diameter of the syringe needle.

The outer contour of the cap 20 presents a generally cylindrical shape of circular cross-section with variations of diameter and of shape as set forth hereinafter.

From the distal end 24, at the level of which the face of the end wall 30 turned towards the outside is substantially planar, there extends a first part 50 in the form of a frustum of a cone of relatively limited extent, a second part 52 of cylindrical shape of slightly flared circular cross-section which extends substantially up to half the proximal end zone 32 at the level of the third portion 44 of the housing 26.

The slightly flared shape of the second part 52 conventionally facilitates unmoulding of the cap and the shape of the first part 50 facilitates centering and assembly of the rigid shell on the cap, as will be explained hereinafter.

A projecting shoulder 54 connects the second part 52 to a third part 56 of cylindrical shape of very slightly flared circular cross-section which extends up to the second portion 42 of the housing 26 near the first portion 40.

Another projecting shoulder 58 connects the third part 56 to a fourth part 60 of truncated shape which extends up to the level of the first portion 40 of the housing 26. This fourth part 60 is extended in the direction of the proximal end of the cap 20 by a fifth part 62 of cylindrical shape of circular cross-section, itself adjacent a sixth part 64 recessed with respect to the fifth part 62. This sixth part 64 comprises a shoulder surface 66 forming an angle very slightly smaller than 90° with respect to the fifth part 62 and an annular face 68 close to the opening 36 and of cylindrical shape of circular cross-section. This sixth part is thus constituted by an annular shoulder 64 re-entrant in the direction of the proximal end 22.

According to an essential characteristic of the present invention, between the first and second portions 40 and 42 of the housing 26, there is provided an annular bead 70 forming an inner swell of matter at the level of the end of the second portion 42 facing the proximal end 22.

This bead 70 advantageously presents, in longitudinal section, the shape of a half drop of water of which the widest part faces the proximal end 22 of the cap 20, the tip of the drop joining the second portion 42 opposite the other projecting shoulder 58.

This bead 70 defines an inner contour of the housing in the form of a half-pear and constitutes a bead for mechanically retaining the distal part of the body of the syringe, as will be explained hereinbelow. Upon passage in the autoclave, the bead 70 guarantees that the distal part 104 of the syringe 100 is retained in the housing 26, even for a considerable pressure difference between the housing 26 and the enclosure of the autoclave. It is only from a great pressure difference $\Delta AP1$ (positive value equal to the difference between the pressure prevailing in the housing 26 and the pressure prevailing in the autoclave enclosure) that the mechanical strength of the bead 70 is not sufficient and would risk a relative displacement between the syringe and the needle protection device.

Figure 2:
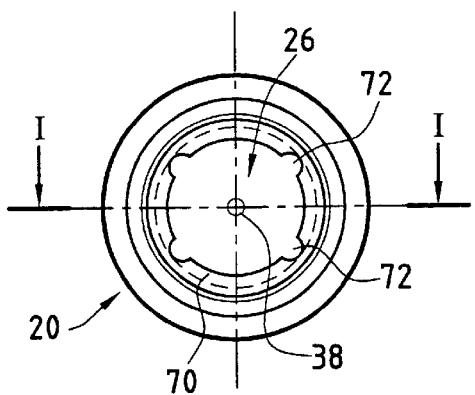
FIG. 2 is an elevation of the device of FIG. 1 in direction II, i.e. from the proximal end of the elastic needle cap.
Figure 3:
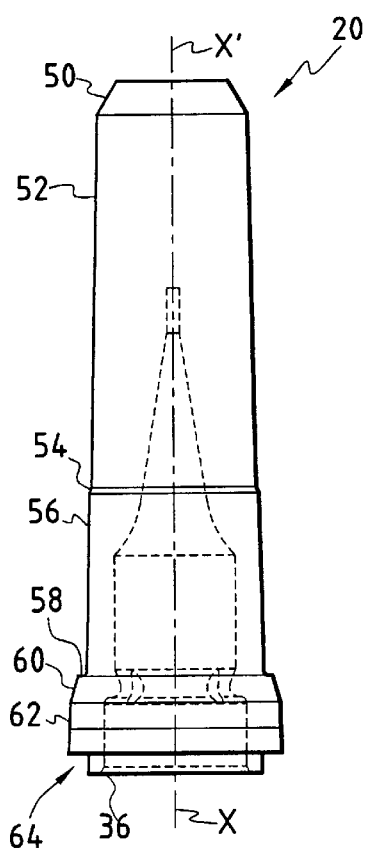
FIG. 3 is a partially transparent view in side elevation of the device of FIG. 1.

In order to facilitate, during passage in the autoclave, the passage of the water vapor under pressure out of the housing 26 from a certain smaller difference in pressure ($\Delta P2<\Delta P1$) and to improve the deformability of this annular bead 70, the latter is provided with four slots 72 extending in longitudinal direction over and into the bead 70, these four slots being regularly distributed angularly and extending only over part of the radial thickness of the bead 70 as may be seen in FIG. 2. Preferably (cf. FIG. 9), the slots 72 extend radially over a depth of the bead 70 generating a diameter between two slots equal to D2.

Figure 9:
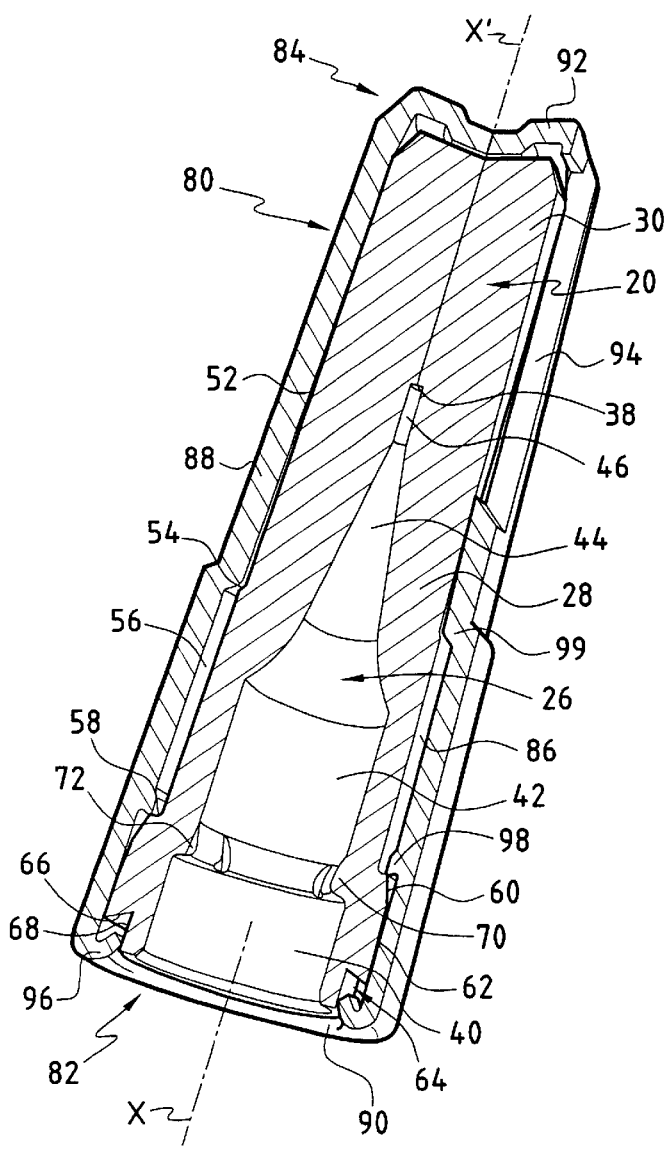
FIG. 9 is a view in perspective and in section in direction IX—IX of FIG. 7 of the needle protection device of FIGS. 6 to 8.

From one to n slots 72 may, of course, be provided, which may present a greater or lesser depth than the case illustrated in FIG. 9. If there is a large number of such slots 72, they separate between them a large number of portions of the bead 70 which each form a small protuberance. Similarly, these slots 72 may be more or less wide than the case illustrated in FIG. 9.

A bead (not shown) may, of course, be provided, which presents another shape, in particular which is not annular. For example, between two slots 72, the bead may present a swollen inner contour in the form of a frustum of a torus whose centre is outside the cap 20.

In this way, it is observed that, at the level of the first and second portions 40 and 42, the diameter of the housing 26 is minimum at the location of the bead 70 and presents a value $D_{min}$.

Figure 4:
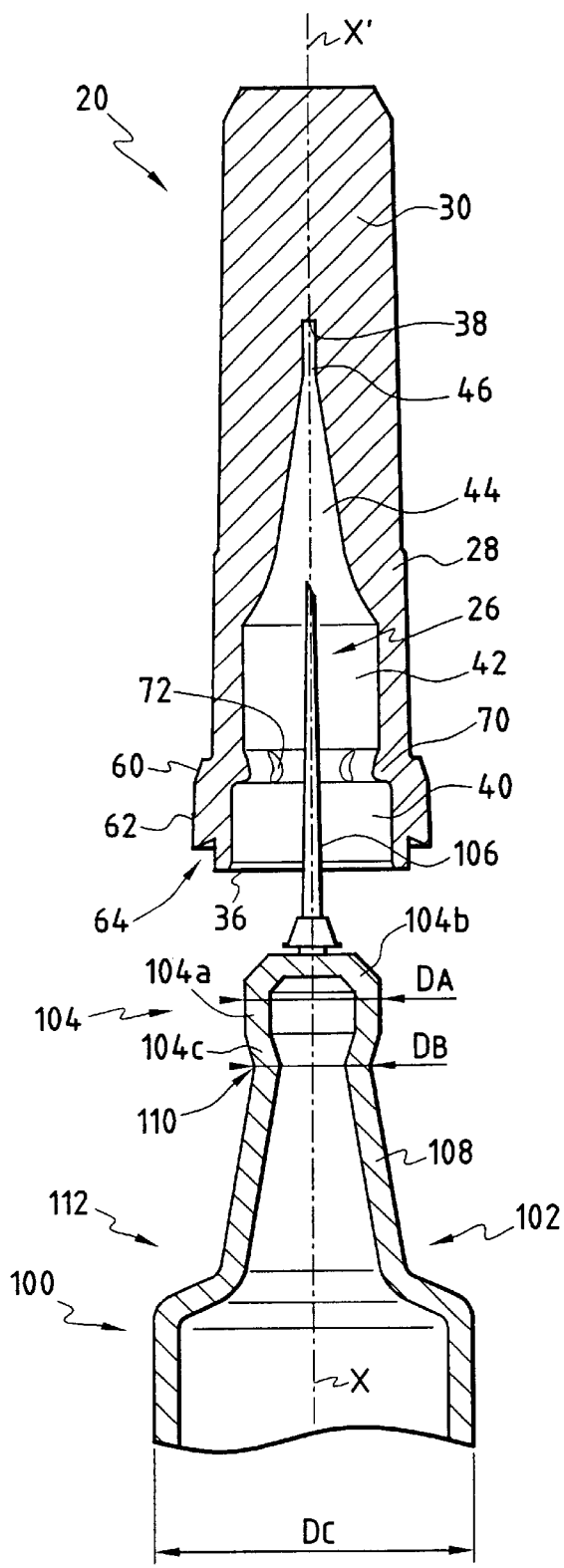
FIG. 4 shows the needle protection device of FIG. 1, slightly in recess with respect to a distal syringe part composed of the distal part of the cylindrical syringe body and of the needle.
Figure 5:
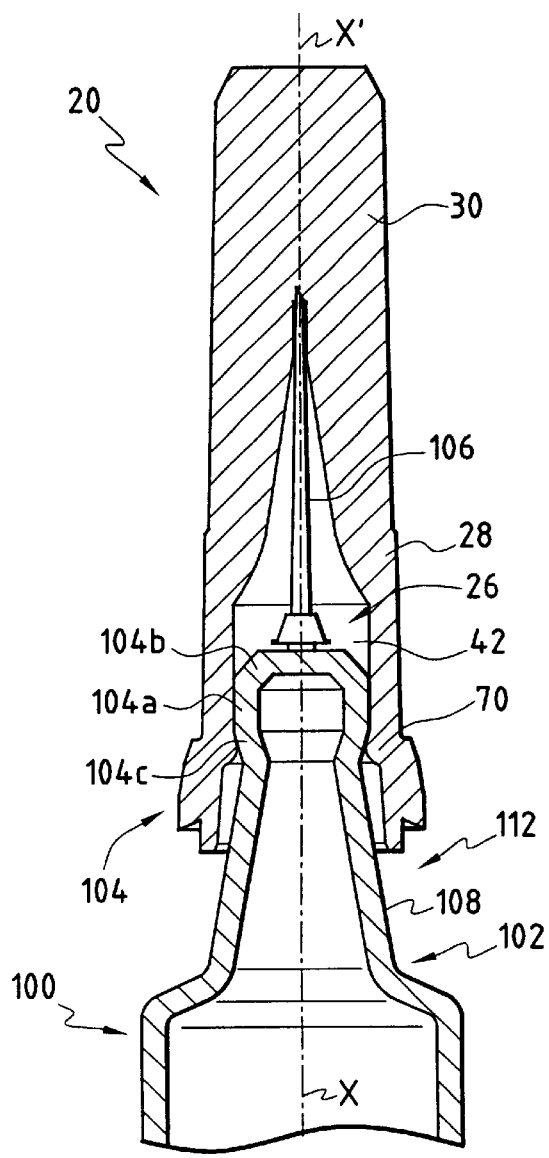
FIG. 5 shows a view in partial longitudinal section of the needle protection device mounted on the syringe.

As may be seen in FIGS. 4 and 5, which partially show a hypodermic syringe 100, the cylindrical body 102 of this syringe is provided with a distal part 104 which bears the needle 106.

This distal part 104 presents a generally spherical shape, constituting a ball bearing the needle 106. More precisely, the distal part 104 forms an annular swell formed by three parts: a terminal truncated part 104b narrowing in the direction of the free end of the needle 106, a median part 104a in the form of a cylinder of circular cross-section of diameter $D_A$ and a truncated joining part 104c. The truncated joining part 104c is adjacent a part of revolution 108 forming an annular depression 110 (of diameter $D_B$) with respect to the widest part of the distal part 104.

As illustrated in FIGS. 4 and 5, when the needle 106 penetrates inside the cap 20, the free end of the needle 106 sticks in the end wall 30 of the cap 20 while the distal part 104 of the body 102 of the syringe penetrates in the housing 26 of the cap 20 at the level of the second portion 42.

As may be seen in FIG. 5, after assembly, the annular bead 70 is located against the truncated joining part 104c, this effecting an efficient mechanical retention of the distal part 112 of the syringe 100, formed by the needle 106 and the cylindrical body 102, inside the housing 26.

Due to the presence of this annular bead 70 which is applied in close contact against the truncated joining part 104c, it is unnecessary for the diameter D2 of the second portion 42 of the housing 26 to ensure considerable tightening about the median part 104a.

However a tight contact must be ensured by the second portion 42 of the housing 26 against the median part 104a of the distal part 104 of the syringe in order to maintain the housing 26 sterile after passage in an autoclave. The tightness in question is a microbiological tightness allowing a sterility to be maintained, i.e. guaranteeing the absence of microbial germs or toxic products of microbial or fungic origin.

The diameter D2 of the second portion 42 of the housing 26 is preferably greater than or equal to 85%, preferably substantially equal to 92%, of the outer diameter $D_A$ of the distal part 104 of the syringe body 102.

Likewise, the diameter $D_{min}$ of the annular bead 70 is preferably included between 85 and 95% of the diameter D2 of the second portion 42 of the housing 26, the minimum diameter $D_{min}$ preferably being substantially equal to 90% of the diameter D2 of the second portion 42.

In particular, tests have been made with a syringe 100 of 1 ml presenting a syringe body 102 of outer diameter $D_C$=8.15 mm, the outer diameter $D_A$ of the spherical zone 104a being equal to 4.35 mm, while the outer diameter $D_B$ of the narrowed zone 104c is equal to 3.85 mm.

For this type of syringe, the cap 20 used presents the following dimensions:

D2 (diameter of the second portion 42 of the housing 26): 4 mm, $D_{min}$ (diameter of the housing 26 at the level of the annular bead 70): 3.6 mm, D1 (diameter of the opening 36 of the housing 26): 4,7 mm.

The afore-mentioned dimensions are given for a cap 20 presenting a total length of 23.5 mm for an outer diameter of 7 mm at the level of the fifth part 62, the fourth part 60 tapering down to a minimum outer diameter of 6.5 mm.

With such a cap, tightness of the housing 26 is obtained which is maintained for the whole cycle of sterilization in the autoclave without any displacement between the cap 20 and the distal part 104 of the syringe.

In effect, the annular bead 70 ensures mechanical blocking of the distal part 104 of the syringe in the second portion 42 of the housing 26 during the passage in the autoclave. In addition, the tight contact ensured by the second portion 42 of the housing 26 against the median zone 104a of the distal part 104 of the syringe creates a microbiological tightness between the housing 26 and the exterior of the protection device during and after passage in the autoclave, which guarantees a permanent sterility of the housing and of the needle until the syringe 100 is used, more precisely up to separation between the cap 20 and the needle 106.

In addition, this embodiment makes it possible to obtain, whatever the initial state of the needle (dry, wet, siliconed), a resistance to the effort for separating the cap 20 from the syringe 100 which is of the order of 9 N, this guaranteeing comfort of use upon opening, this value being lower than for the prior art products and in any case lower than the maximum force of tear admissible, which is of the order of 35 N.

As illustrated in FIGS. 6 to 10, the present invention also relates to a protection device for syringe needle which comprises, in addition to the elastic cap 20 described hereinabove, a rigid shell 80 in which the cap 20 is housed.

This type of shell 80 is conventionally used for reinforcing the protection of the user of the syringe against the needle pricking him/her, by offering an additional outer rigid protection which is difficult for the needle 106 to pierce.

This rigid shell 80 presents a general longitudinal cylindrical shape, of circular cross-section, it is mounted coaxially with respect to the cap 20 and it extends between an open proximal end 82 and a closed distal end 84.

The rigid shell 80 is dimensioned to allow the insertion and blocking of the cap 20 therein. To that end, the cavity 86 defined by the inner contour of the rigid shell 80 presents a shape which substantially follows the outer shape of the cap 20.

The rigid shell 80 is composed of a longitudinal wall 88 which extends from the proximal end 82 at the level of the opening 90 up to the distal end 84 at the level of which the longitudinal wall 88 extends by a terminal wall 92 which closes the cavity 86.

The longitudinal wall 88 is provided, between the terminal wall 92 and about two fifths of the length of the longitudinal wall, with four cut-outs 94 intended to allow passage of the water vapor under pressure from the enclosure of the autoclave up to the housing 26.

These four cut-outs 94 are (cf. FIGS. 7 and 8) of generally longitudinal shape and are distributed radially at 90° with respect to one another.

In order to retain the cap 20 inside the cavity 86 of the rigid shell 80, cap retaining means are provided, comprising a preferably annular re-entrant edge 96, which forms an element, preferably a flange, projecting inwardly of the cavity 86.

This re-entrant flange 96 is therefore housed in the shoulder formed by the sixth part 64 of the outer contour of the cap 20, with the result that the cap 20 is prevented from leaving the shell 80 by the axial abutment of the re-entrant flange 96 on the shoulder surface 66.

During assembly, when the cap 20 is driven in the shell 80 to a maximum, the essentially planar outer face of the end wall 30 of the cap 20 comes into axial abutment against the inner face of the terminal wall 92 of the shell 80. On the contrary, in normal position, there is no contact between the outer face of the end wall 30 of the cap 20 and the inner face of the terminal wall 92 of the shell 80.

In addition, in order to complete the blocking of the relative movement in longitudinal translation between the cap 20 and the rigid shell 80, more particularly the movement of the cap 20 in the direction of the terminal wall 92 of the shell 80, there is provided, as additional retaining means, an annular rib 98 disposed on the inner face of the longitudinal wall 88 of the shell 80. This annular rib 98 is adapted to cooperate with the outer face of the lateral wall 28 of the cap 20 by coming into abutment against the shoulder 58 of the cap 20.

This shoulder 58 forms a first re-entrant shoulder in the direction of the distal end 24 of the device, this first shoulder 58 being located on the outer face of the lateral wall 28 of the cap 20 opposite the second portion 42 of the housing 26.

Figures 6, 8:
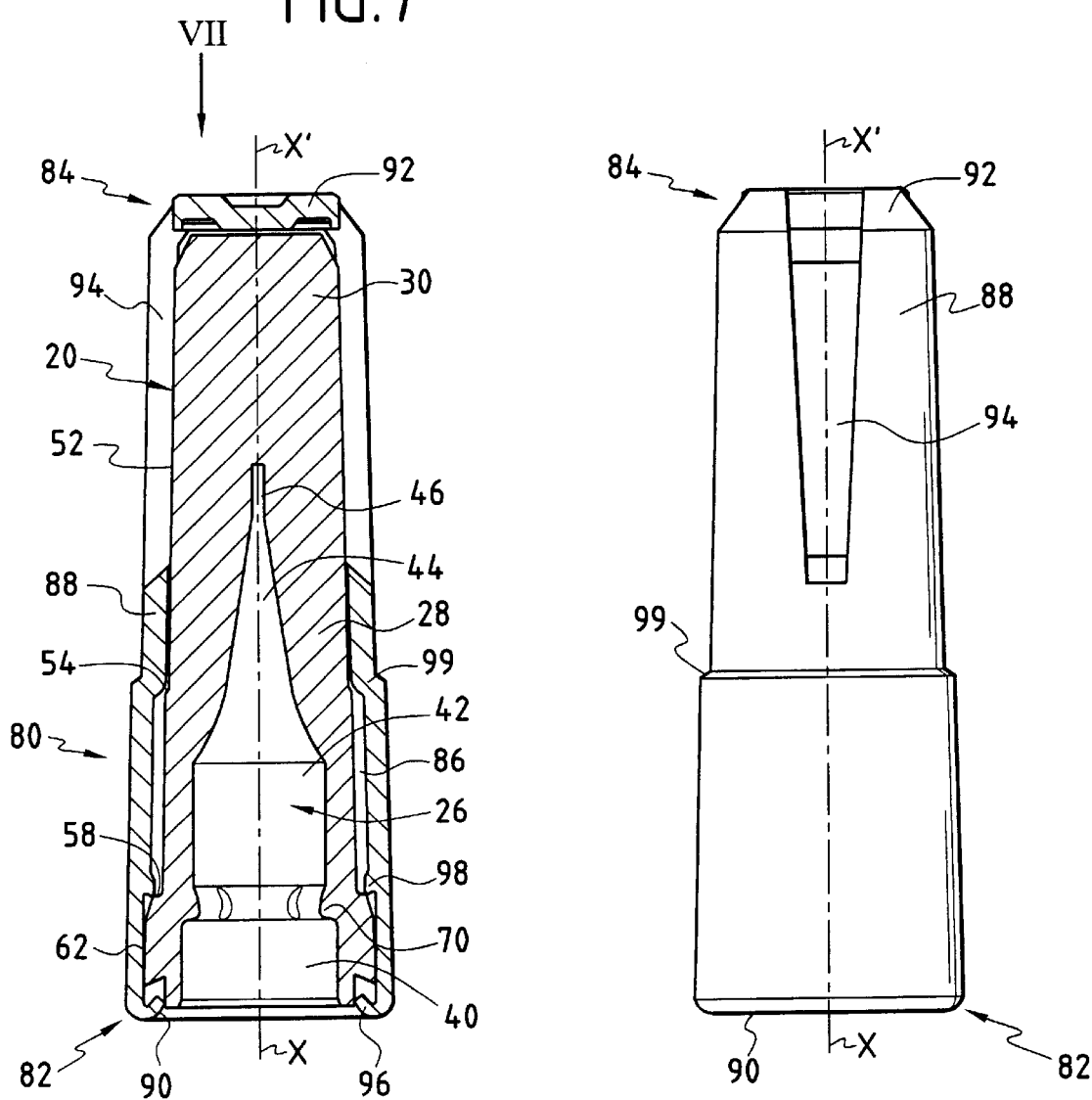
FIG. 6 shows a view in diametral longitudinal section of another form of embodiment of the needle protection device comprising, in addition to the elastic needle cap, a rigid shell.
FIG. 8 is a view in longitudinal elevation of the protection device of FIG. 6.

As may be seen in FIG. 6, the longitudinal wall 88 comprises, about half-way along the shell 80, at least on its outer face, and preferably (case illustrated) over the whole thickness of the longitudinal wall 88 of the shell 80, an annular re-entrant shoulder 99 in the direction of the distal end 24 of the device (the inner diameter of the cavity 86 being smaller on the side of the shoulder 99 located nearest the terminal wall 92).

This re-entrant shoulder 99 is formed so as to be located opposite the shoulder 54 of the cap 20 which forms a second re-entrant shoulder in the direction of the distal end of the device, being located on the outer face of the lateral wall 28 of the cap 20 opposite the third section 44 of the housing 26.

Figure 7:
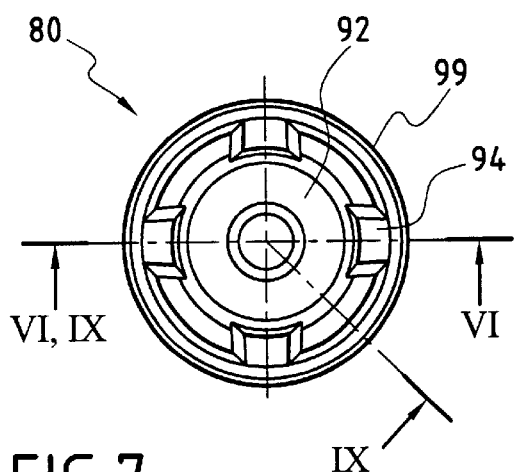
FIG. 7 is a view in elevation in direction VII of FIG. 6, i.e. from the distal end of the needle protection device.

As may be seen in FIGS. 7 and 8, the re-entrant shoulder 99 lies both on the inner face and on the outer face of the longitudinal wall 88 so as to form an annular setback of this wall.

The particular purpose of this annular shoulder 99 is to facilitate manipulation of the needle protection device by the different machines of the production and assembly line.

Figure 10:
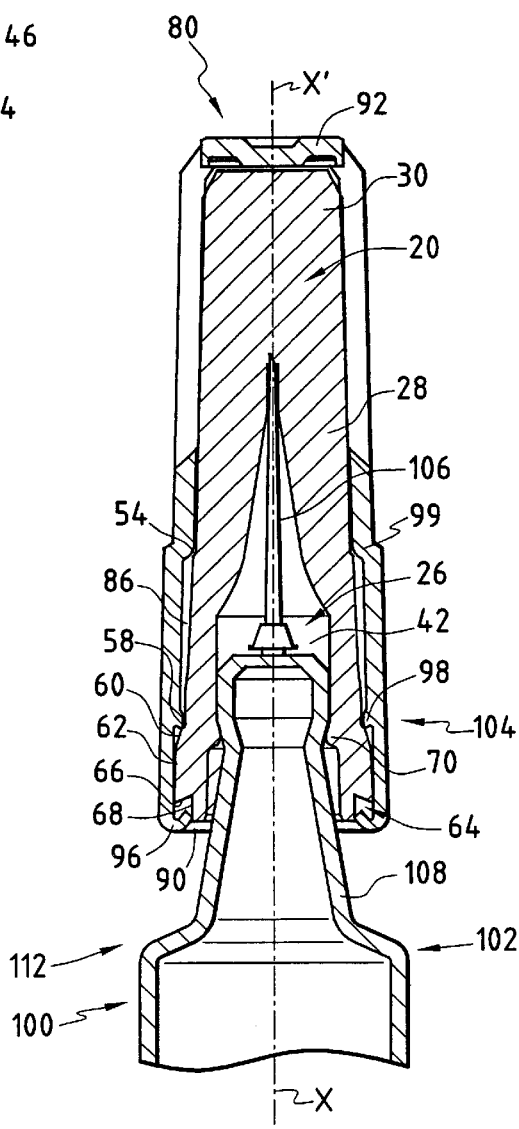
FIG. 10 is a view in diametral longitudinal section of the needle protection device of FIG. 6 mounted on a syringe.

As may be seen in FIG. 10, in the case of the cap 20 being contained in the rigid shell 80, the protection device thus formed may be mounted on a syringe 100 in the same way as with the cap 20 alone.

In addition, when the cap 20 is inserted inside the cavity 86 of the shell 80, there exists a contact between the fifth part 62 of the outer contour of the cap 20 and the inner face of the longitudinal wall 88 located between the rib 98 and the flange 96.

At the moment of insertion of the distal part 104 of the body 102 of the syringe in the housing 26, there is compression of the annular bead 70 by the distal part 104 of the body 102 of the syringe. The lateral wall 28 of the cap being made of a sufficiently supple material (for example rubber), part of the deformation is absorbed by the slots 72.

On the other hand, the lateral wall 28 of the cap presenting a sufficiently small thickness opposite the fourth part 60 of the outer contour of the cap 20, the deformation of the annular bead 70 creates a radial spacing apart of the lateral wall 28 at that spot, hence a deformation of the fourth part 60 which comes closer to the inner face of the cylindrical longitudinal wall 88 of the shell 80: this is rendered possible thanks to the outer shape, in the form of a frustum of a cone, of the fourth part 60 of the lateral wall 28 which is located opposite the annular bead 70 and to the annular space available on the inner face of the longitudinal wall 88 of the shell 80 opposite this fourth part 60.

It will be understood that the fourth part 60 might also present the form of a frustum of a cone upturned with respect to the one illustrated, i.e. a shape narrowing in the direction of the proximal end 22 of the cap.

This fourth part 60 might also present a shape different from that of a frustum of a cone, provided that this surface creates, once the cap is housed in the shell, a free annular space between it and the zone opposite it of the longitudinal wall 88 of the rigid shell 80. In effect, this annular space makes it possible to receive a part of the outward radial deformation of the zone of the lateral wall 28 of the cap 20 which is located against the median part 104a of the distal part 104 of the syringe (cf. FIG. 10).

More generally, a space preferably exists, advantageously annular as shown in FIGS. 6, 9 and 10, between the longitudinal wall 88 of the rigid shell 80 and the lateral wall 28 of the cap 20, which extends longitudinally along axis (X, X') from the cut-outs 94 up to the annular rib 98 disposed on the inner face of the longitudinal wall 88 of the shell 80, i.e. up to the projecting shoulder 58, on either side of the shoulder 99. This space allows the passage of the water vapor under pressure from the enclosure of the autoclave up to the housing 26 thanks to the permeability to gases, particularly to pressurized water vapor, of the material constituting the cap 20. Moreover, that part of this space which surrounds the second portion 42 of the housing 26 also makes it possible to receive the radial expansion of the zone of the lateral wall 28 of the cap 20 which surrounds the median part 104a of the distal part 104 of the syringe (cf. FIG. 10).

It will thus be understood that the presence of the shell in no way modifies the use and functioning of the cap 20 for sterilization during passage in an autoclave and for maintaining sterility of the syringe 106 after passage in the autoclave. In addition, the presence of the shell does not modify the resistance to the effort for separating the cap 20 from the syringe 100, while increasing the user's protection against being pricked.

Shapes other than those illustrated in the Figures are, of course, possible for the cap 20 and for the shell 80.

What is claimed is:

1. A device for protecting a syringe needle comprising an elastic needle cap of generally longitudinal direction presenting a closed distal end and an open proximal end, said cap being formed by a lateral wall extending from said proximal end along a proximal end zone, defining an inner housing adapted to receive the distal part of the body of a needle syringe, and by an end wall whose thickness extends from said distal end along a distal end zone, said end wall being capable of being pierced through a part of its thickness by the free end of said needle, said housing comprising, from said proximal end:
an opening presenting a maximum diameter,
a first portion of truncated or cylindrical shape, of circular cross-section,
a second cylindrical portion of circular cross-section presenting a diameter smaller than said maximum diameter and intended to house the distal part of the syringe body which bears said needle, and
a third portion which narrows from said second portion in the direction of a back of said housing,
wherein said lateral wall is further provided with an annular bead disposed in said housing between said first and second portions of said housing, at least one slot extending longitudinally in said annular bead.

2. The device of claim 1, wherein said bead presents in longitudinal cross-section the shape of a half drop of water of which the widest part faces the proximal end of the cap.

3. The device of claim 1, wherein, at the level of the first and second portions, the diameter of the housing is minimum at the location of said bead, said minimum diameter being included between 85 and 95% of said diameter of said second portion.

4. The device of claim 3, wherein said minimum diameter is substantially equal to 90% of said diameter of said second portion.

5. The device of claim 1, wherein said cap is of revolution about a longitudinal axis.

6. The device of claim 1, wherein four slots regularly distributed angularly extend in the longitudinal direction over said annular bead.

7. The device of claim 1, wherein said diameter of said second portion is greater than or equal to 85% of the outer diameter of the distal part of the syringe body.

8. The device of claim 1, wherein said diameter of said second portion is substantially equal to 92% of the outer diameter of the distal part of the syringe body.

9. The device of claim 1, wherein an outer face of the lateral wall which surrounds said annular bead is in the form of a frustum of a cone.

10. The device of claim 1, wherein it further comprises a rigid shell general longitudinal and cylindrical shape, of circular cross-section, presenting an open proximal end and an at least partially closed distal end, said shell comprising a longitudinal wall extending from said proximal end up to said distal end and a terminal wall located at its distal end, said shell being intended to surround and contain aid elastic needle cap and being provided with means for retaining said cap.

11. The device of claim 10, wherein said retaining means comprise a re-entrant annular flange forming the proximal free end of the shell and presenting a inner diameter adapted to retain in the shell the proximal end of the lateral wall of the cap.

12. The device of claim 11, wherein the proximal end of the outer surface of the lateral wall of the cap comprises a re-entrant annular shoulder in the direction of the proximal end of the device and adapted to cooperate with said annular flange.

13. The device of claim 11, wherein said retaining means further comprises an annular rib disposed on the inner face of the longitudinal wall of the shell and adapted to cooperate with a first re-entrant shoulder in the direction of the distal end of the device and located on the outer surface of the lateral wall of the cap opposite the second portion of said housing.

14. The device of claim 10, wherein the longitudinal wall of the shell presents, at least on its outer face, a re-entrant annular shoulder in the direction of the distal end of the device.

* * * * *